(12) United States Patent
Roberto et al.

(10) Patent No.: US 8,617,159 B2
(45) Date of Patent: Dec. 31, 2013

(54) SURGICAL INSTRUMENTATION FOR PERFORMING ENDOLUMINAL AND/OR TRANSLUMINAL ANASTOMOSIS

(75) Inventors: Tacchino Roberto, Rome (IT); Federico Bilotti, Latina (IT); Alessandro Pastorelli, Rome (IT); Brian James Thompson, Cincinnati, OH (US); Michele D'Arcangelo, Rome (IT)

(73) Assignee: Ethicon Endo-Surgery, Inc., Cincinnati, OH (US)

( * ) Notice: Subject to any disclaimer, the term of this patent is extended or adjusted under 35 U.S.C. 154(b) by 967 days.

(21) Appl. No.: 12/438,783

(22) PCT Filed: Jul. 20, 2007

(86) PCT No.: PCT/EP2007/057500
§ 371 (c)(1),
(2), (4) Date: Aug. 27, 2009

(87) PCT Pub. No.: WO2008/028725
PCT Pub. Date: Mar. 13, 2008

(65) Prior Publication Data
US 2012/0330296 A1    Dec. 27, 2012

(30) Foreign Application Priority Data
Sep. 8, 2006    (EP) .................................... 06018863

(51) Int. Cl.
*A61B 18/14* (2006.01)
(52) U.S. Cl.
USPC ............................................. 606/47; 600/104
(58) Field of Classification Search
USPC ......... 606/41, 45–50; 600/104, 130; 604/174, 604/175, 510, 514, 516
See application file for complete search history.

(56) References Cited

U.S. PATENT DOCUMENTS 5,112,310 A * 5/1992 Grobe ........................... 604/175
7,316,655 B2    1/2008 Garibotto et al.
(Continued)

FOREIGN PATENT DOCUMENTS

| DE | 9107166 U1 | 9/1991 |
| DE | 102004015223 A1 | 10/2005 |
| WO | WO 2006/048906 A | 5/2006 |

OTHER PUBLICATIONS

EPO Search Report dated Mar. 10, 2009 for corresponding patent application, European Patent Application No. PCT/EP2007/057500.

*Primary Examiner* — Michael Peffley

(57) ABSTRACT

An instrumentation for performing an endoluminal or transluminal anastomosis, comprises an anastomotic ring device including a proximal ring (5) having two guide wire seats (22) adapted to slidably receive two guide wires (1, 2) and a distal ring (6) having two guide wire seats (25) adapted to slidably receive the two guide wires (1, 2), the proximal ring 5 and the distal ring 6 being snap-connectable to each other, a surgical probe (7) comprising an elongate insertion shaft (30) and a probe head (32) adapted to be endoluminally advanced to a proximal tissue portion (3), the insertion shaft (30) defining guide wire canals (8, 9) extending into two guide wire exit openings (31) defined in the probe head (32) and adapted to deliver the distal ends (1″, 2″) of said guide wires (1, 2) to said proximal tissue portion (3). The distance between the two guide wire exit openings (31) of the probe (7) is substantially equal to the distance between the two guide wire seats (22) of the proximal ring (5) and to the distance between the two guide wire seats (25) of the distal ring (6).

18 Claims, 14 Drawing Sheets

(56) References Cited

U.S. PATENT DOCUMENTS

| | | |
|---|---|---|
| 7,637,919 B2 | 12/2009 | Ishikawa et al. |
| 7,727,200 B2 * | 6/2010 | Suzuki .......................... 604/171 |
| 8,182,459 B2 * | 5/2012 | Dann et al. .................... 604/500 |
| 2006/0271075 A1 | 11/2006 | Bilotti et al. |
| 2011/0004146 A1 * | 1/2011 | Priplata et al. .................... 604/8 |

* cited by examiner

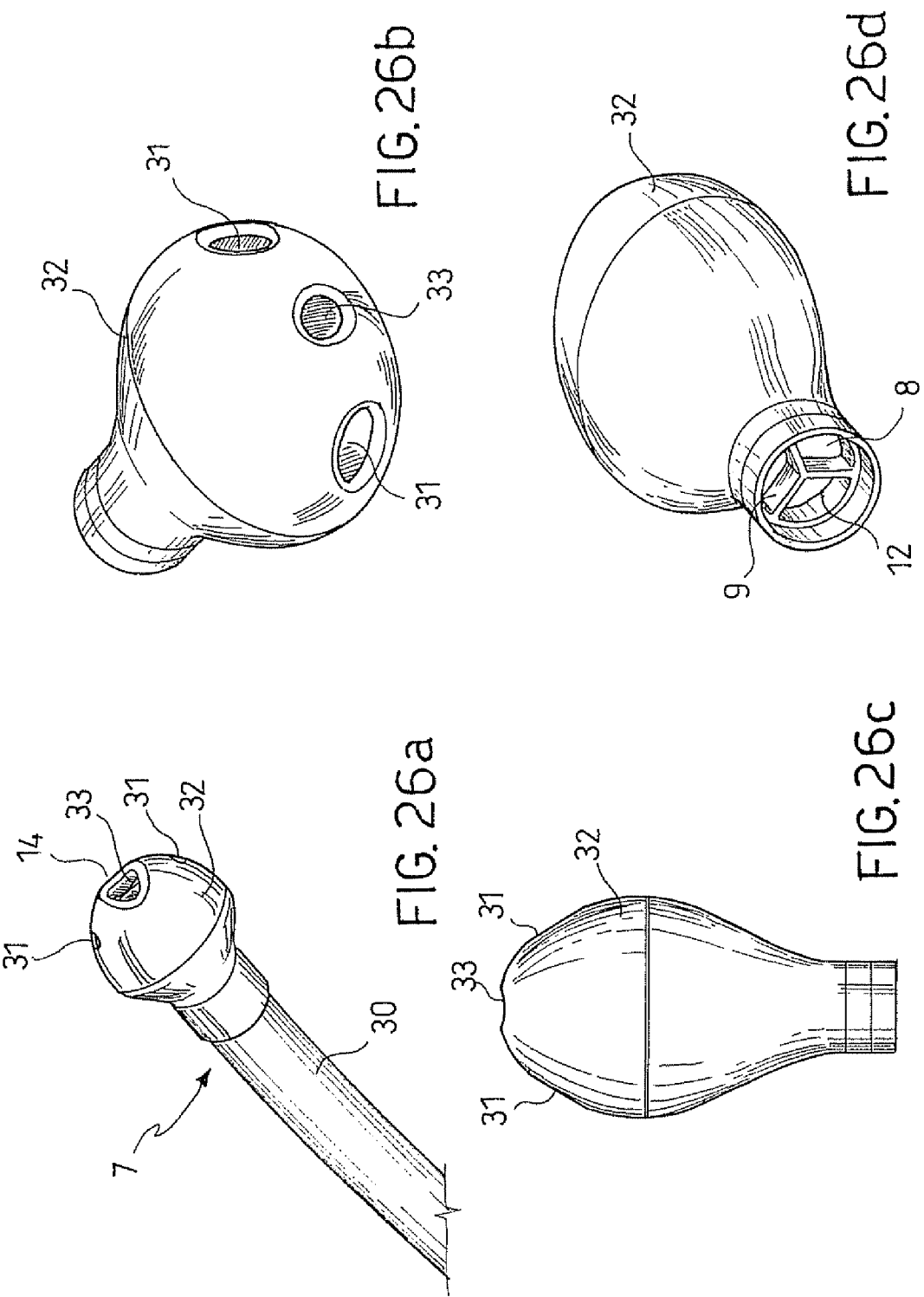

SURGICAL INSTRUMENTATION FOR PERFORMING ENDOLUMINAL AND/OR TRANSLUMINAL ANASTOMOSIS

The present invention relates, in general, to devices and methods for surgically modifying organs and vessels and more particularly to a surgical instrument and method for performing an endoluminal and or transluminal anastomosis, particularly of the digestive tract, such as gastro-jejunostomy, jejuno-jejunostomy or similar interventions as for example colo-proctostomy, jejuno-colostomy or anastomoses involving the Chole duct, by applying an anastomotic ring device comprising two snap-connectable rings.

The known surgical methods and instruments for performing the above mentioned anastomoses by applying anastomotic ring devices involve traditional open surgery or laparoscopic surgical techniques, which are rather invasive and require the use of quite complex and cumbersome surgical devices. As a result the risk of post-operative complications is undesirably high.

Alternative pure endoluminal or endoscopic methods and devices have been developed by the inventors which are not free from drawbacks, since neither the instrumentation nor the methods are mature enough to provide the necessary guidance and control of the instruments inside the body in order to adequately approximate the tissue portions to be joined in anastomosis and to precisely align and join the rings of the anastomotic ring device in the anastomotic site. As a result operative and post operative complications cannot be excluded.

A further drawback of the pure endoscopical approach to anastomosis lays in the fact that endoscopy requires a skill and experience which can be acquired only by long term learning. Therefore, such endoscopical anastomoses can be reliably performed by only a few surgeons.

The object of the present invention is therefore to propose a surgical method for performing an endoluminal or transluminal anastomosis, particularly of the digestive tract, which is less invasive than the currently employed open surgery approaches and, at the same time, allows for a better control and instrumentation guidance than the endoscopical methods, in order to reduce the risk of post-operative complications.

A further object of the present invention is to configure the proposed method in a way to reduce its dependency from the surgeons endoscopical skill and experience.

A yet further object of the invention is to provide a surgical instrumentation especially developed and adapted to perform the proposed method.

These and other objects are achieved by a kit of surgical instruments according to claim 1 and by the method described in the following description. Advantageous embodiments are claimed in the dependent claims.

For better understanding the invention and appreciating the related advantages, a detailed and non limiting description of embodiments is provided with reference to the accompanying drawings, in which.

Figure 25B:
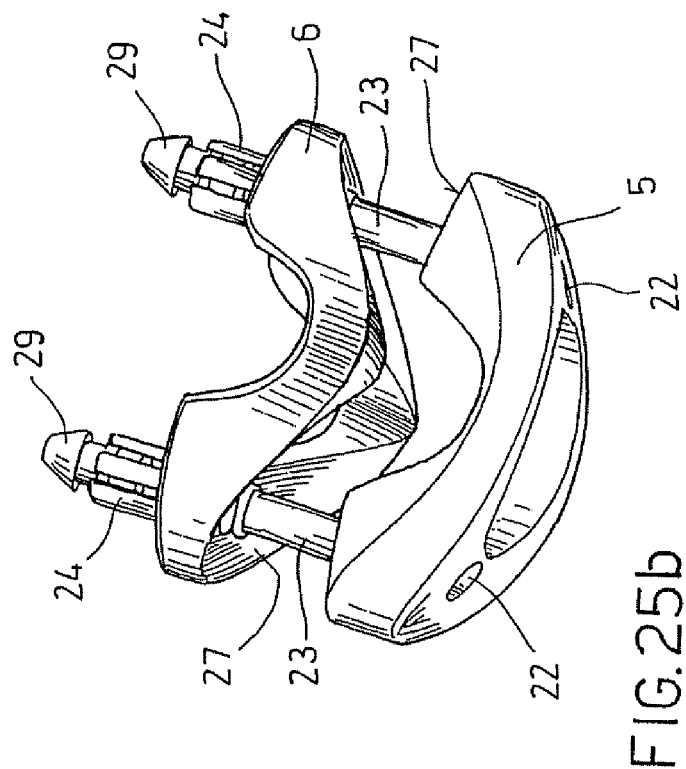
Figure 25A:
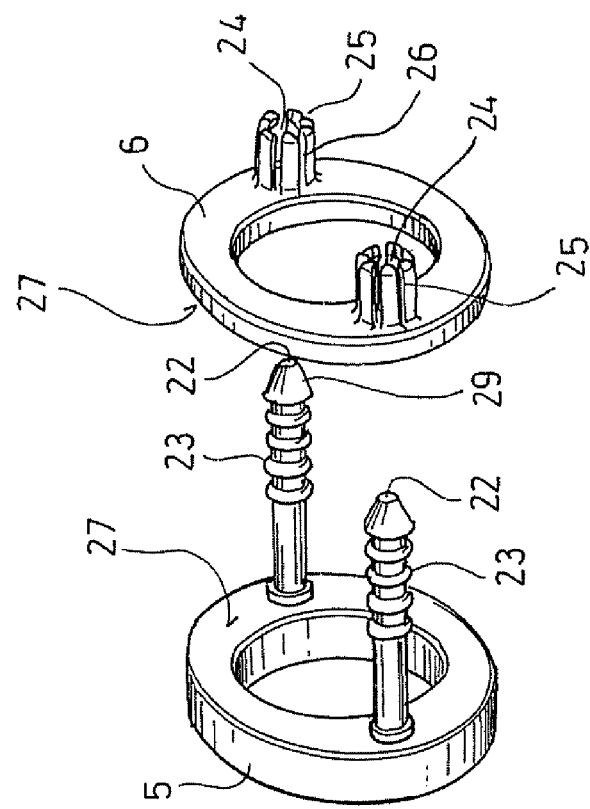

FIGS. 25*a* and 25*b* are perspective views of an anastomotic ring device of the instrumentation according to the invention;

FIGS. 26*a*, 26*b*, 26*c* and 26*d* are perspective views of a surgical probe and its distal probe head according to the invention.

For the sake of clarity and for better evidencing the technical effect of the features of the surgical instrumentation according to the invention and its interaction with the particular environment of application, the following detailed description of the invention will first deal with the surgical method thought up by the inventors and subsequently describe the surgical instruments for carrying out the method.

Overall Procedure to Perform the Anastomosis

According to the invention, a method for performing an endoluminal or transluminal anstomosis, such as e.g. a gastro-jejunostomy, a jejuno-jejunostomy, a colo-proctostomy, a jejuno-colostomy or anastomoses of the chole duct, comprises generally the following steps:

Creating a loop of guide wire means by placing guide wire means 1, 2 in the body of a patient in a way that the guide wire means 1, 2 extend from an extracorporeal proximal end 1', 2' into the body where it goes through a proximal tissue portion 3 and through a distal tissue portion 4 which are planned to be joined in anastomosis and out of the body up to an extracorporeal distal end 1", 2" (FIGS. 1-11). In the following, if not otherwise specified, the terms "proximal" and "distal" are referred to the directions along the guide wire loop and to the above defined proximal and distal ends thereof.

Fixing a proximal ring 5 of an anastomotic ring device to the proximal end 1', 2' of the guide wire means 1, 2 and delivering the proximal ring 5 to the proximal tissue portion 3 by pulling the distal extracorporeal end 1", 2" of the guide wire means 1, 2 in a distal direction until the proximal ring 5 reaches the proximal tissue portion 3 (FIGS. 12-15), Slidably connecting a distal ring 6 of the anastomotic ring device to the distal end 1", 2" of the guide wire means 1, 2 and pushing it proximally along the guide wire means until it reaches the distal tissue portion 4 (FIGS. 16-18), Contemporaneously pulling the distal end 1", 2" of the guide wire means 1, 2 distally and pushing the distal ring 6 proximally to approximate the proximal and distal rings, thereby tearing the proximal and distal tissue portions 3, 4 situated upon the guide wire means between the distal and proximal rings 5, 6 in contact to another (FIG. 19, 20), Snap-connecting the distal ring 6 with the proximal ring 5, thereby clamping the distal and proximal tissue portions between them (FIG. 19, 20), Cutting the tissue internally overhanging the anastomotic ring device to open the anastomotic lumen, Pulling the proximal end 1', 2' of the guide wire means 1, 2 to remove the guide wire means 1, 2 from the body.

The loop of the guide wire means 1, 2 starts and ends either in natural orifices, like mouth, nose, anus or, alternatively, in artificially created openings in the body, such as colostomy, abdominal incisions, wound or fistulas. Preferably, the guide wire means 1, 2 enters and exits the body through natural ducts (e.g. mouth). While the guide wire means can comprise one or more single flexible guide wires, it is preferable to provide two guide wires 1, 2 which penetrate the proximal and distal tissue portion in a substantially equal preset distance in a way to allow an axial and angular alignment of the distal and proximal ring of the anastomotic ring device.

Creation of the Loop of the Guide Wire Means

In accordance with an important aspect of the invention, the loop of the guide wire means 1, 2 is created by means of the following procedural steps:

Transluminally (e.g. transorally) introducing a slender surgical probe 7 through the proximal inlet port (e.g. mouth) for the guide wire means 1, 2 and pushing the probe 7 from outside the body distally towards the proximal tissue portion 3 (e.g. a jejunal anstomotic site), Transporting the distal end 1", 2" of the guide wire means 1, 2 to the proximal tissue portion 3 through one or more guide wire canals 8, 9 formed in the probe 7 and perforating the proximal tissue portion 3 with the guide wire ends 1", 2" or needle guide wire ends in a way that the distal guide wire ends 1", 2" protrude distally from the proximal tissue portion 3 (e.g. into the previously $CO_2$ insufflated abdominal space 10), Removing the surgical probe 7 from the body by pulling it proximally out of the proximal inlet port (e.g. mouth) and leaving the guide wire means 1, 2 in place, Transluminally introducing the same probe 7 or a different slender surgical probe through the distal inlet port for the guide wire means which might but need not coincide with the proximal inlet port (e.g. mouth) and pushing the probe 7 from outside the body proximally (with reference to the loop direction) towards the distal tissue portion 4 (e.g. the gastric wall tissue), Transporting a snare 11, preferably a radio frequency current electrode snare, to the distal tissue portion 4 through an instrument delivery canal 12 formed in the probe 7 and perforating the distal tissue portion 4 by transmitting radiofrequency current from the RF snare 11 to the tissue, subsequently passing the snare 11 through the perforation in a way that the snare 11 protrudes proximally from the distal tissue portion 4 in the same space where the distal guide wire ends 1", 2" lay (e.g. in the previously $CO_2$ insufflated abdominal space 10), Feeding the distal end 1", 2" of the guide wire means 1, 2 through the snare hole and catch the distal end 1", 2" of the guide wire means by the snare 11, subsequently pulling the snare 11 together with the distal end 1", 2" of the guide wire means 1, 2 distally through the perforation of the distal tissue portion 4 (e.g. gastric wall) and distally withdrawing the probe 7 and the snare 11 together with the distal guide wire ends 1", 2" through the distal inlet port (e.g. transorally) out of the body.

Advantageously, the transluminal introduction of the probe 7 to the proximal tissue portion 3 is assisted by laparoscopic manipulating the natural duct (e.g. jejunum), moving it over the probe 7 in a direction against the advancing direction of the probe 7, e.g. by means of a proximal milking movement of the natural duct against the distal pushing direction of the probe 7 using a laparoscopic grasper 13.

In case of a gastro-jejunostomy, the probe 7 needs to be advanced transorally through the esophagus and the stomach and across the pylorus into the duodenum, which is not always easy to point at with a normal surgical probe. During this step of the procedure an Ewald tube might be pushed through the patients mouth down the esophagus into the stomach and the probe 7 can be advantageously guided inside the Ewald tube until and across the pylorus.

Similarly, the perforation of the proximal tissue portion 3 is advantageously assisted by laparoscopically tearing the proximal tissue portion 3 (e.g. the jejunum) against a distal tip 14 of the probe 7 defining an exit port for the guide wire means 1, 2 or guide wire needle in a way that the distal guide wire ends 1", 2" can poke through the tissue 3 in a stable and controlled manner. For instance the proximal tissue portion 3 is folded back proximally over the probe tip 14 by means of the laparoscopic grasper 13, while the probe 7 is pushed distally against the fold formed in the proximal tissue 3.

In accordance with a yet further advantageous embodiment, the radiofrequency snare 11, after having pierced through the distal tissue portion 4 is advanced into the space containing also the distal end 1", 2" of the guide wire means 1, 2 (e.g. the $CO_2$ insufflated abdomen 10) under laparoscopic visualization by a laparoscope 20 and the distal end 1", 2" of the guide wire means 1, 2 is caught by the snare 11 by grasping the guide wire ends 1", 2" with a laparoscopic grasper 13 and inserting them with the grasper 13 in the snare hole under laparoscopic visualization by laparoscope 20. With reference to the deployment of the anastomostic ring device, also the transport of the proximal ring 5 to the proximal tissue portion 3 is advantageously assisted by laparoscopic manipulation, e.g. local straightening or milking movement of the natural duct (e.g. small intestine 15) through which the proximal ring 5 advances towards the anastomotic site.

The distal ring 6 is advantageously pushed proximally along the guide wire means by a customized semi-rigid deployment probe 19, in which the deployment probe 19 itself can be preferably guided by the same guide wire means 1, 2.

When the proximal inlet port (e.g. mouth) coincides with the distal outlet port of the guide wire loop and when different portions 1', 2'; 1", 2" of the loop meet in same intracorporeal spaces (as for example inside the stomach 16), it will be necessary to separate the different loop portions at least along the tracts where they overlap, in order to reliably prevent guide wire mix up and confounding. Preferably, also the extracorporeal proximal and distal ends of the guide wire means 1, 2 are separated in order to allow the surgeon to immediately identify the correct guide wire ends to pull, to insert or to withdraw as required by the procedure. Advantageously, two visually distinguishable flexible guide wire sheaths, i.e. a proximal sheath 17 and a distal sheath 18, are provided and placed extra-corporeally over the distal 1", 2" and proximal 1', 2' guide wire ends and advanced inside the body as far as necessary to separate the guide wire portions in the zones of overlap.

As can be readily appreciated from the foregoing description, the combination of transluminal or endoscopic placement of the guide wire loop and delivery of the anastomotic ring device with laparoscopically assisting the guide wire placement and the ring deployment makes it possible to perform an anastomosis with comparatively cost effective instrumentation, which will be described in the following, and at the same time increases the precision of the surgical intervention without using invasive open surgery techniques. The proposed method can be seen as a mixed endoscopic-laparoscopic approach which reconciles in a synergic manner the need to increase the precision of the performance of the anastomosis (pure endoscopic approaches are not yet sufficiently mature to guarantee the required precision), to reduce invasiveness (typical disadvantage of the traditional open surgery) and to reduce the dependency of the result from the experience and skill of the surgeon (only a few specialists are able to perform reliably precise endoscopic operations). In the following, a set of surgical instruments will be described which has been especially developed and adapted for performing an anastomosis in accordance with the proposed method.

The instrumentation comprises advantageously one or more of the following components:
   the proximal and distal anastomotic rings 5, 6,
   the two guide wires 1, 2;
   the surgical probe 7
   the laparoscopic grasper 13,
   the snare 11,
   the proximal sheath 17 and distal sheath 18,
   a laparoscopic illumination/visualization device 20,
   connecting crimpers 21,
   a surgical deployment probe 19.

Detailed Description of the Anastomotic Ring Device

FIGS. 25a and 25b show an anastomotic ring device with the proximal ring 5 and the distal ring 6 which is not only but particularly adapted to perform a gastro-jejunostomy according to the previously described method. The proximal ring 5 (or bowel ring 5) is adapted to bear against the proximal tissue portion 3 (jejunal tissue), while the distal ring 6 (or gastric ring 6) is adapted to bear against the distal tissue portion 4 (gastric tissue) opposite the proximal tissue portion 3 and the proximal ring 5. The proximal ring 5 comprises two seats 22 each adapted to receive one of the two guide wires 1, 2 respectively, in which the two seats 22 are arranged or formed at a distance thereby allowing to align the proximal ring 5 with the guide wire means and to fix the angular position of the proximal ring 5 with respect to the two guide wires 1, 2 of the guide wire means. In this way the proximal ring 5 can be precisely positioned and angularly aligned with respect to the first tissue portion 3, which is preferably perforated and penetrated by the two guide wires 1, 2 at approximately the same distance as the distance between the two seats 22 of the proximal ring.

Moreover, the proximal ring 5 comprises snap connecting means suitable to snap engage corresponding counter-snap connecting means of the distal compression ring 6. The snap connecting means comprise at least two snap connecting portions 23 arranged at a distance which is substantially equal to a distance of corresponding counter-snap connecting portions 24 of the distal ring 6, thereby assuring a correct angular alignment of the proximal and distal ring when connected. The correct alignment of the proximal and distal rings during approximation is assured by the fact that the distal ring 6 comprises two sliding seats 25 for slidably receiving the two guide wires 1, 2, in which the distance between the two sliding seats 25 is equal to the distance between the two guide wire seats 22 of the proximal ring 5.

In accordance with the embodiments illustrated in FIGS. 25a and 25b, the snap connecting portions 23 of the proximal ring 5 are embodied as two distally protruding diametrically oppositely arranged and substantially parallel toothed or recessed 43 pins, while the counter-snap connecting portions 24 of the distal ring 6 are embodied as two diametrically oppositely arranged substantially parallel tubular toothed seats which are radially elastically deformable, e.g. due to longitudinal slots 26, and adapted to snap engage the pins 23 in different longitudinal positions corresponding to different axial distances between the proximal and distal compression rings 5, 6. This makes it possible to use the anastomotic ring device for different tissue thicknesses and enables the surgeon to vary the pressure on the clamped tissue portions 3, 4. Preferably, the counter-snap connecting portions 24 of the distal ring 6 protrude distally from a distal surface of the distal ring 6 opposite its tissue pressure surface 27.

The pressure surfaces 27 of the proximal and distal rings 5, 6 destined to contact and clamp the proximal and distal tissue portions 3, 4 are substantially plane (FIG. 25a) or circumferentially wavy (FIG. 25b) in order to increase the circumference of the anastomotic lumen with respect to the external ring circumference. Advantageously, the pressure surfaces 27 are roughened or locally profiled in order to prevent the tissue 3, 4 to squeeze radially out of the ring device in response to the axial pressure.

In accordance with a preferred embodiment, the guide wire seats 22 of the proximal ring 5 are defined axially inside the snap pins 23 and the sliding seats 25 of the distal ring device 6 are defined inside the tubular counter snap seats 24, thereby aligning the axes of ring positioning and guidance with the axes of ring snap connection.

Moreover, the toothed pins 23 of the proximal compression ring 5 include pointed free ends 28 suitable to penetrate the proximal and, possibly, the distal tissue through the same guide wire passage holes.

Detailed Description of the Surgical Probe

Figure 3:
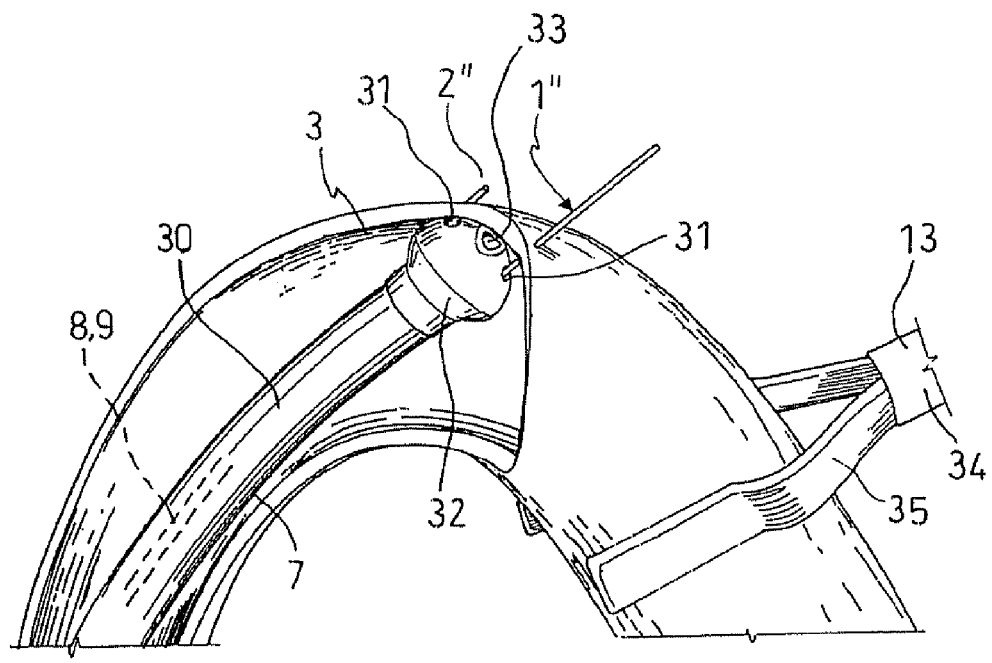
Figure 4:
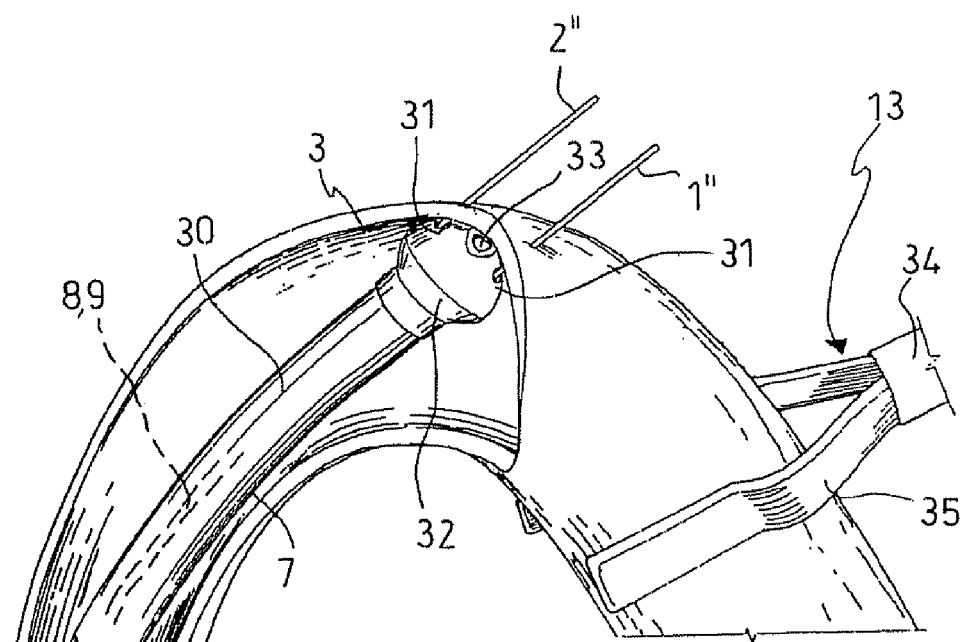
Figure 5:
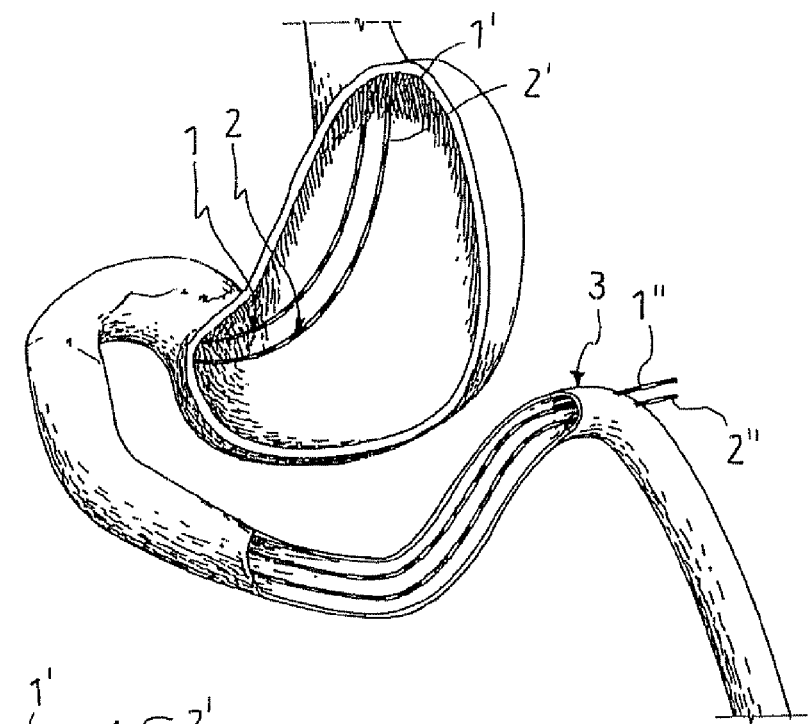

The surgical probe 7 illustrated for instance in FIGS. 3 and 4 comprises a slender elongate flexible, but longitudinally incompressible insertion shaft 30 defining preferably one or more internal canals 8, 9, 12 (depicted by a dashed line) for slidably receiving the two guide wires 1, 2 and, possibly, other surgical instruments and allowing their transport through the insertion shaft 30 until a distal probe head 32. The distal probe head 32 comprises a spherical, ellipsoid or substantially egg shaped smoothly rounded housing which defines internal canals for slidably housing the two guide wires 1, 2 and, possibly, additional surgical instruments, as well as two distinct exit openings 31 for the guide wires 1, 2.

The rounded shape of the probe head 32 prevents tissue trauma during insertion and allows to advance the probe 7 through the often very tortuous natural ducts, e.g. the gastric-jejunal region of the digestive tract.

The guide wire exit openings 31 are arranged on a substantially distal end face of the probe head 32 and spaced apart from one another at a distance substantially equal to the distance of the guide wire seats 22 of the proximal ring 5 and of the sliding guide wire seats 25 of the distal ring 6, so that the distance of the guide wires 1, 2 exiting from exit openings 31 is at least approximately equal to the distance of the guide wire seats of the anastomotic ring device 5, 6. Thanks to this particular configuration, the geometry of the probe 7 assures that during penetration of the proximal tissue portion 3, the distance between the distal guide wire ends 1", 2" and, hence, the distance between the holes poked in the proximal tissue 3 is equal to the distance of the guide wire seats and connecting portions of the compression rings 5, 6, thereby enabling a correct positioning of these devices. Advantageously, the head 32 of the probe 7 defines a third exit opening 33 which allows to use the very same probe 7 also for transporting the snare 11 to the anastomotic site. The third exit opening 33 is advantageously arranged centrally between the two guide wire exit openings 31.

Detailed Description of the Laparoscopic Grasper

Figure 1:
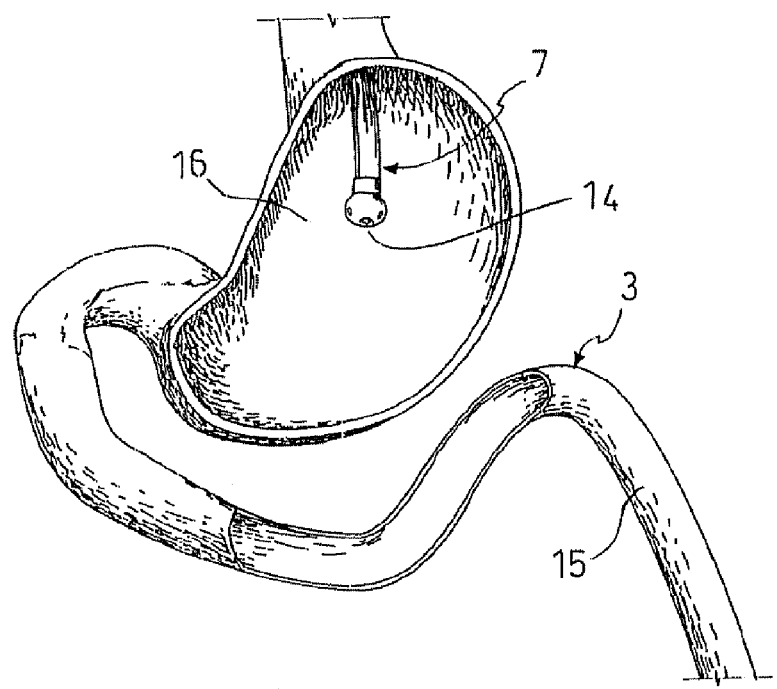
FIG. 1 is a perspective partially sectioned view of a portion of the stomach and of the small intestine subject to a step of a method for creating a guide wire loop according to the invention.
Figure 2:
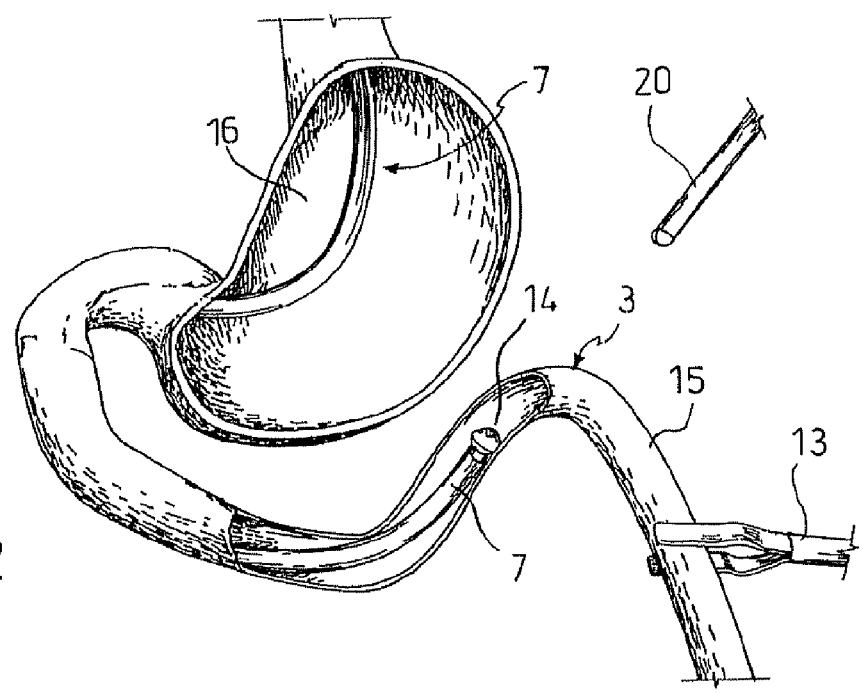
FIGS. 2 to 11 illustrate subsequent steps of the method, as well as a surgical probe and guide wire means for creating the guide wire loop according to the invention.

The laparoscopic grasper 13 is illustrated in FIGS. 2, 3 and 4 and comprises a rigid elongate insertion shaft 34, a distal jaw portion 35 (referred to the surgeons point of view) and a proximal handle portion (not shown) which houses also an actuation mechanism for the jaw portion 35. The jaw portion 35 is preferably dimensioned so that it can open wider than the external diameter of the insertion shaft 30 of the probe 7, in order to enable the surgeon to assist the insertion of the probe 7 by a milking movement of the natural duct (e.g. jejunum) over the probe 7.

Detailed Description of the Connecting Crimpers

Figure 12:
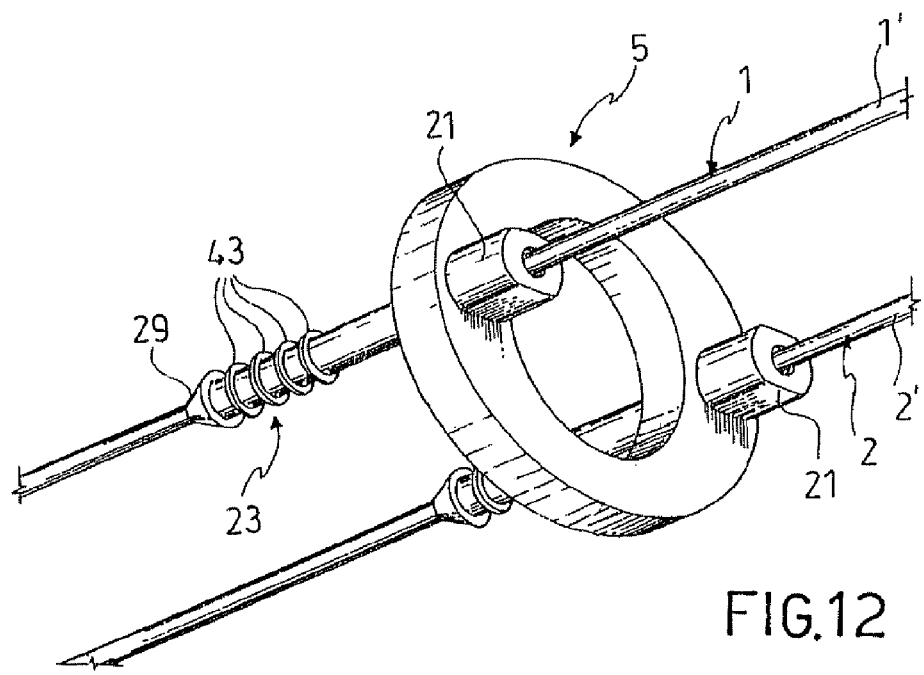
FIG. 12 is a perspective view of a proximal ring of an anastomotic ring device connected to a guide wire means according to the invention.

A preferred embodiment of the connecting crimpers 21 is illustrated in FIG. 12. The crimpers 21 are preferably irreversibly deformable or elastically applicable clips for crimping the guide wires 1, 2. Once the guide wires 1, 2 are inserted through the guide wire seats 22 of the proximal ring 5, the crimpers 21 are applied to the guide wires proximally adjacent to the proximal ring 5 in order to prevent the proximal ring 5 to slide proximally along the guide wire but allow the guide wires 1, 2 to be proximally withdrawn from the proximal ring 5. For this reason the crimpers 21 have an external dimension greater than the passage opening defined by the seats 22 of the proximal ring 5.

Detailed Description of the Snare

According to a preferred embodiment, the snare 11 (FIG. 8, 9) is or comprises a radio frequency electrode suitable to transmit RF current to the adjacent tissue in order to dissect it and coagulate bleeding. For this reason the snare is connected to an RF current conductor wire which in turn is connectable to an extracorporeal radio frequency current generator (not shown). The snare 11 is configured and dimensioned in such a way that the snare hole can receive contemporaneously the two distal guide wire ends 1", 2".

Detailed Description of the Laparoscopic Illumination and Visualization Device

The laparoscopic illumination and visualization device (FIG. 2) is preferably embodied as a rigid shaft laparoscope provided with an illuminating source, e.g. light emitting optical fiber ends, and with a visualization device, e.g. a microcamera or lens suitable to transmit images of the intra-corporeal site on a monitor placed outside the body of the patient.

Detailed Description of the Proximal Sheath and Distal Sheath

The proximal sheath 17 and distal sheath 18 are flexibly deformable tubular devices which are sufficiently longitudinally stiff to allow them to be pushed over the guide wire means 1, 2 inside the body. The proximal and distal sheaths 17, 18 define an internal passage opening dimensioned to receive contemporaneously two guide wires 1, 2 and are distinguished by different colors or visual markings in order to enable the surgeon to easily identify the different guide wire ends 1', 2', 1", 2".

Detailed Description of the Surgical Deployment Probe

A preferred embodiment of the surgical deployment probe 19 is illustrated in FIGS. 16 to 21. The deployment probe 19 comprises a preferably semi-rigid elongate shaft 36 and a distal connector 37 (referred to the surgeons point of view) which is detachably connectable to the distal end of the elongate shaft 36. According to an embodiment, the elongate shaft 36 is provided by a visualization device such as a gastroscope or, alternatively, by a semi-rigid surgical probe without visualization features. The distal connector 37 comprises a proximal coupling portion 38 adapted to detachably snap engage, shape fit, or interference fit with the distal end of the elongate shaft 36. Preferably, the coupling portion includes a plurality of elastic fins protruding in proximal direction (referred to the surgeons point of view) and suitable to elastically embrace and snap connect the elongate shaft 36. The connector 37 further comprises a distal push surface 39 arranged opposite the elastic fins and adapted to contact a corresponding surface of the distal ring 6 in order to push the latter proximally along the guide wire means 1, 2 into snap engagement with the proximal ring 5. The push surface 39 is at least partially complementary with the corresponding surface of the distal ring 6 in a way that the ring 6 can be captively received by said push surface 39. To that end, the push surface 39 delimits one or more cavities 40 configured to receive with interference the distally protruding counter-snap connecting portions 24 of the distal ring 6. While it has been already described that the distal ring 6 is provided with sliding seats 25 for slidably receiving the guide wire means 1, 2, thereby allowing the ring 6 to be pushed in a guided manner along the guide wires 1, 2, according to a preferred embodiment, also the connector 37 include similar sliding seats, preferably opposite radially protruding portions 41 defining longitudinal through holes 42 adapted to slidably receive the guide wires 1, 2 so that both, the distal ring 6 and the deployment probe 19, i.e. the connector 37, can be slidably guided along the distal part of the guide wire loop. The sliding seats 41 are preferably arranged in axial alignment with the cavities 40, so that, in an assembled configuration, the sliding seats 25 of the distal ring 6 and the sliding seats 41 of the connector 37 (which have substantially the same distance from another) are also axially aligned.

The use of the kit of surgical instruments according to the invention for performing an anastomosis through the method according to the invention will be described in the following by means of a non-limiting example of a gastro-jejunostomy via transoral access.

Figure 6:
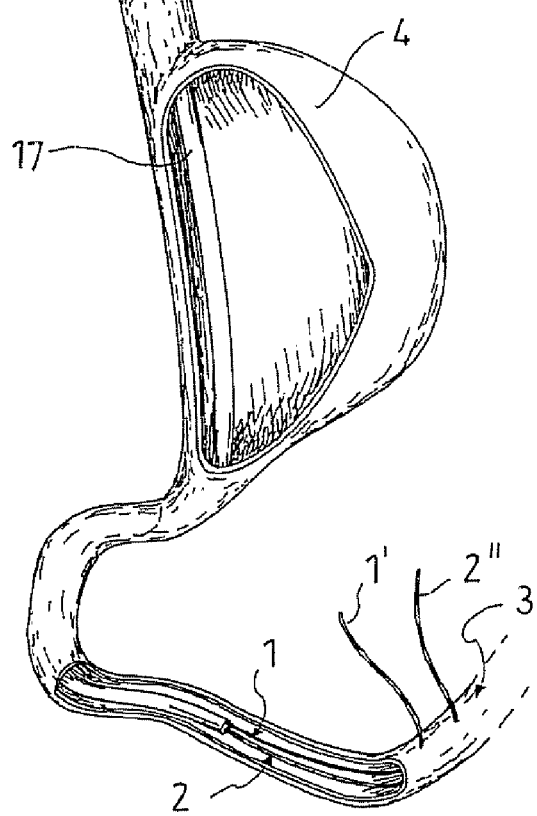
Figure 7:
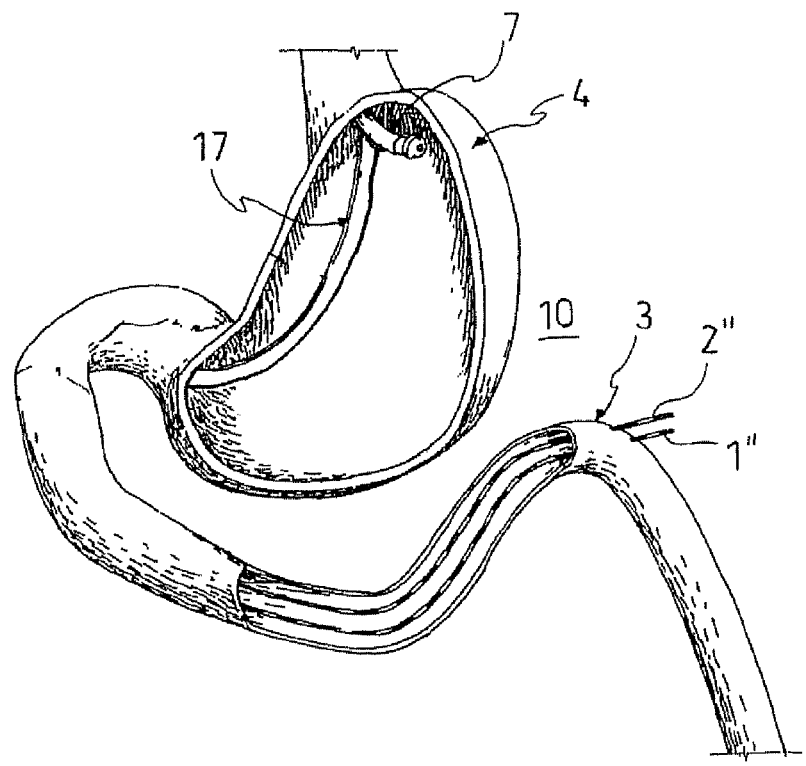
Figure 8:
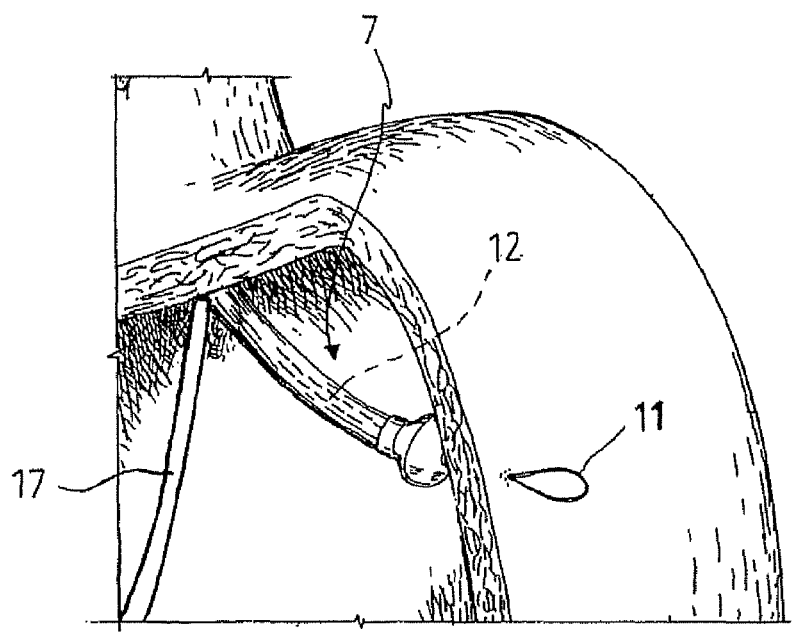
Figure 9:
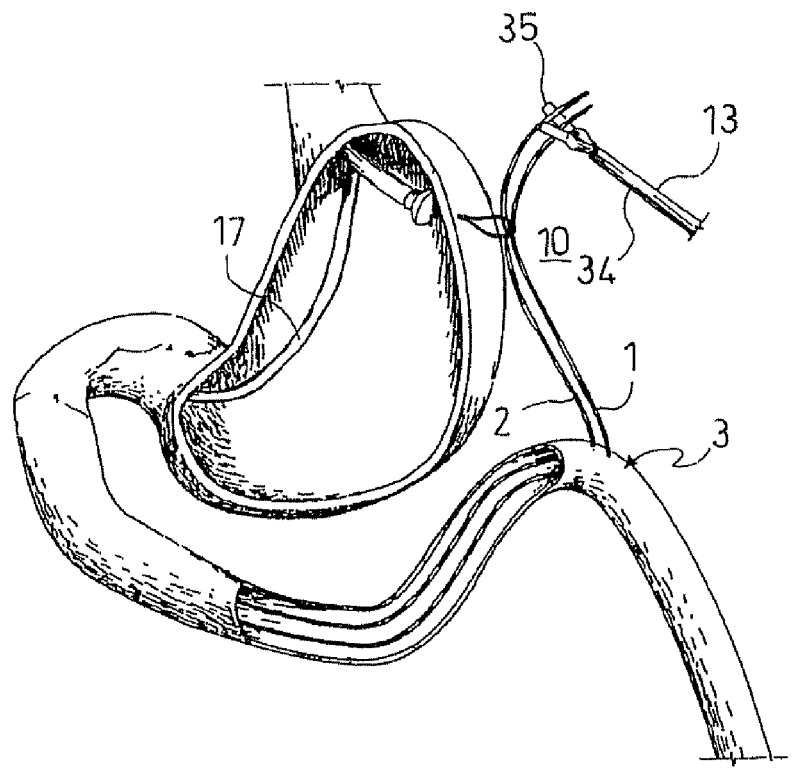
Figure 10:
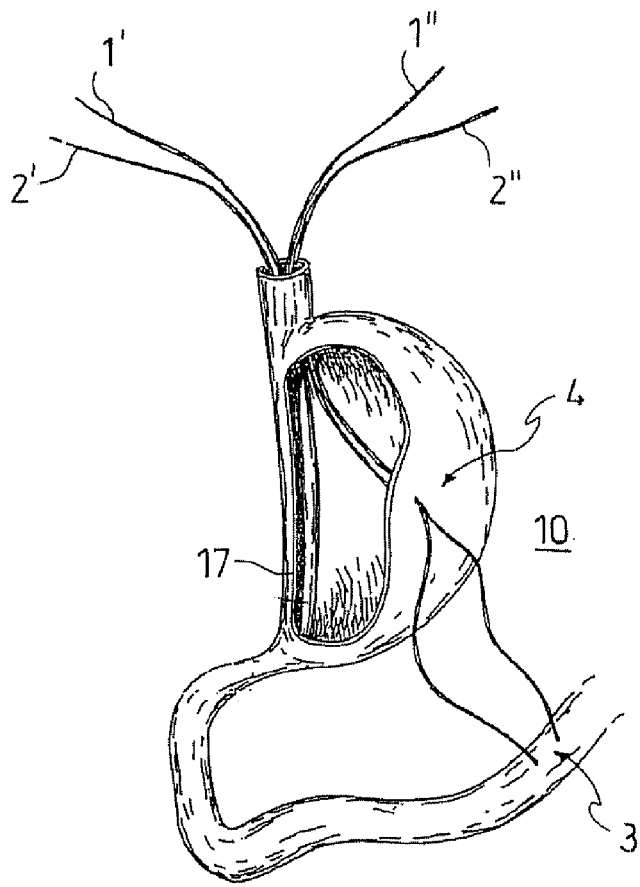
Figure 11:
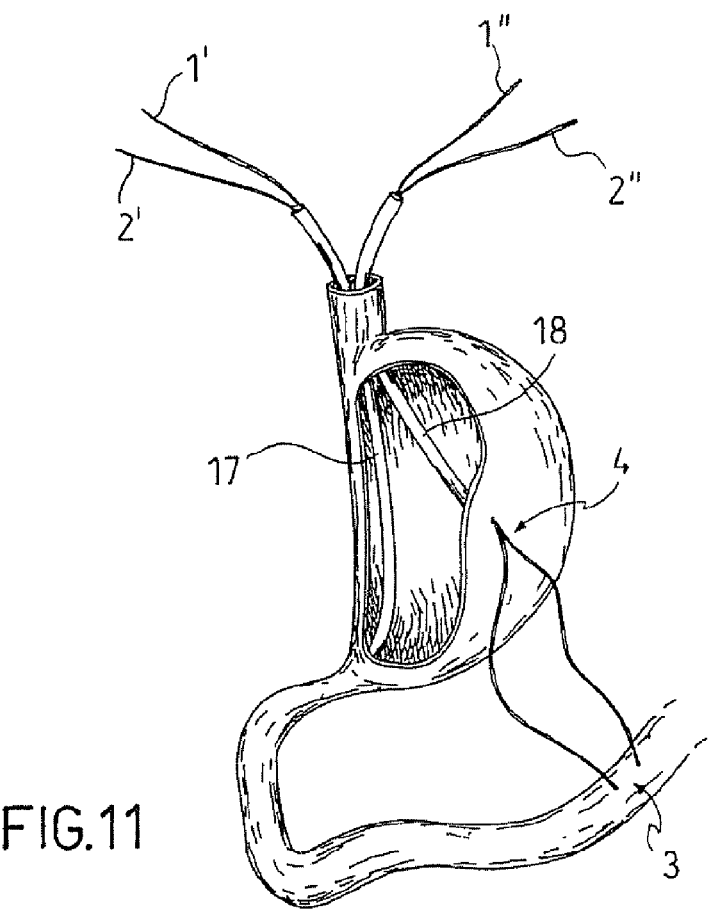

A loop of two single guide wires 1,2 is created by transorally introducing the surgical probe 7 to the desired jejunal anastomotic site by simultaneously pushing the probe 7 from outside the body and manipulating the jejunum over the probe 7 using the laparoscopic grasper 13. Once the head 32 of the probe 7 has reached the anstomotic site, the jejunum is folded proximally over the probe head 32 so that the proximal (jejunal) tissue 3 adheres to the probe head 32. Now the distal guide wire ends 1", 2" are distally advanced out of the guide wire openings 31 against the jejunal tissue 3 in order to perforate the latter in two points having a distance corresponding to the distance between the two guide wire openings 31 of the probe head 32. The distal guide wire ends 1", 2" are then pushed through the jejunal wall into the previously $CO_2$ insufflated abdominal space 10. Then, the surgical probe 7 is removed from the body and guide wires 1, 2 are left in place within the gastro intestinal tract. In this step the distal ends 1", 2" of the guide wires 1, 2 might be grasped by the laparoscopic grasper 13, while the probe 7 is proximally withdrawn (FIGS. 1 to 5). In order to avoid confusion between the different guide wire portions, the proximal sheath 17 is placed extra-corporeally over the proximal guide wire ends 1', 2' and transorally advanced in distal direction at least beyond the pylorus, thereby covering the whole guide wire tract extending through the gastric cavity (FIG. 6). After the placement of the proximal sheath 17, the surgical probe 7 is reintroduced transorally to the desired anastomotic site within the gastric cavity (FIG. 7) and the snare 11 is advanced through the elongate shaft of the probe 7 and out of the instrument exit opening 33. A hole is created in the distal (gastric wall) tissue portion 4 by energizing the RF snare 11 and advancing it through the gastric wall into the abdomen 10 (FIG. 8) under laparoscopic visualization by means of the laparoscope 20. After having de-energized the snare 11, the distal guide wire ends 1", 2" are grasped by the laparoscopic grasper 13 and fed from below into the hole of the snare (FIG. 9). The snare 11, after having caught the distal guide wire ends, is pulled distally through the hole in the gastric wall 4 and transorally out of the patients body together with the probe 7 (FIG. 10). The distal guide wire ends 1", 2" extending transorally out of the patients body are now covered by the distal sheath 18 which is proximally (with respect to the loop) advanced until the gastric anastomotic site (FIG. 11). At this point, two visually distinguished sheaths separate and identify the created guide wire loop.

Figure 13:
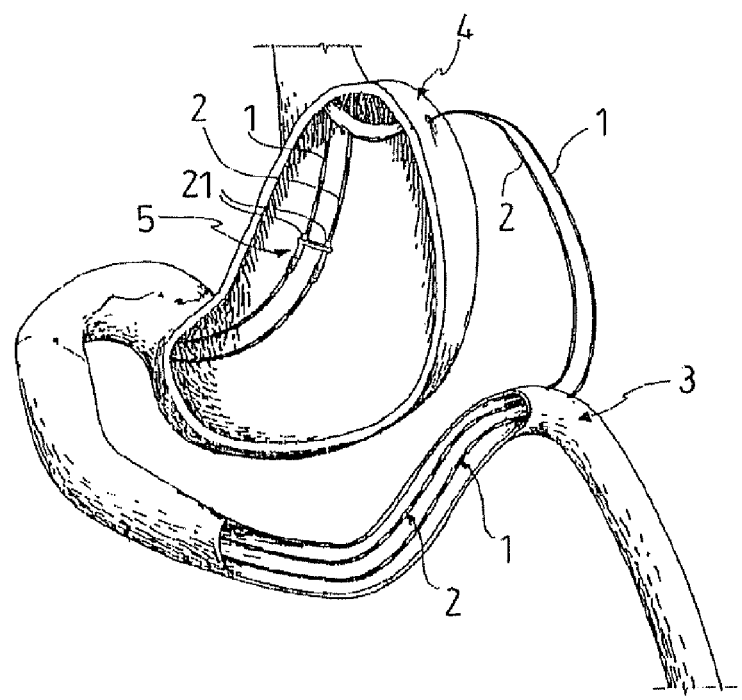
FIGS. 13 to 15 illustrate steps of a method for delivering the proximal ring to a proximal tissue portion according to the invention.
Figure 14:
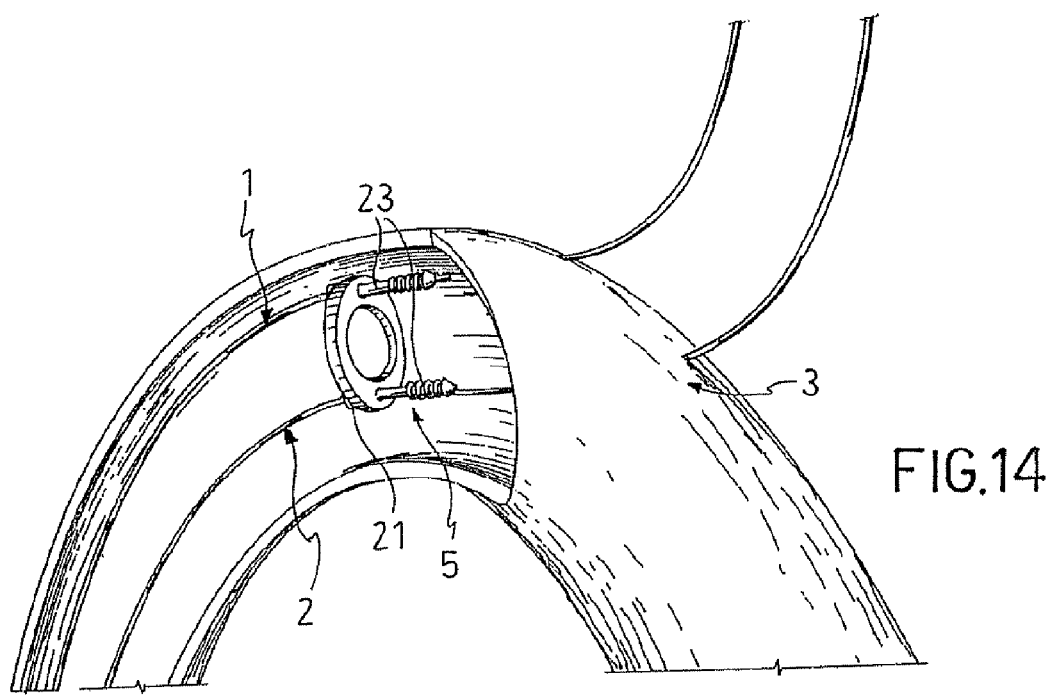
Figure 15:
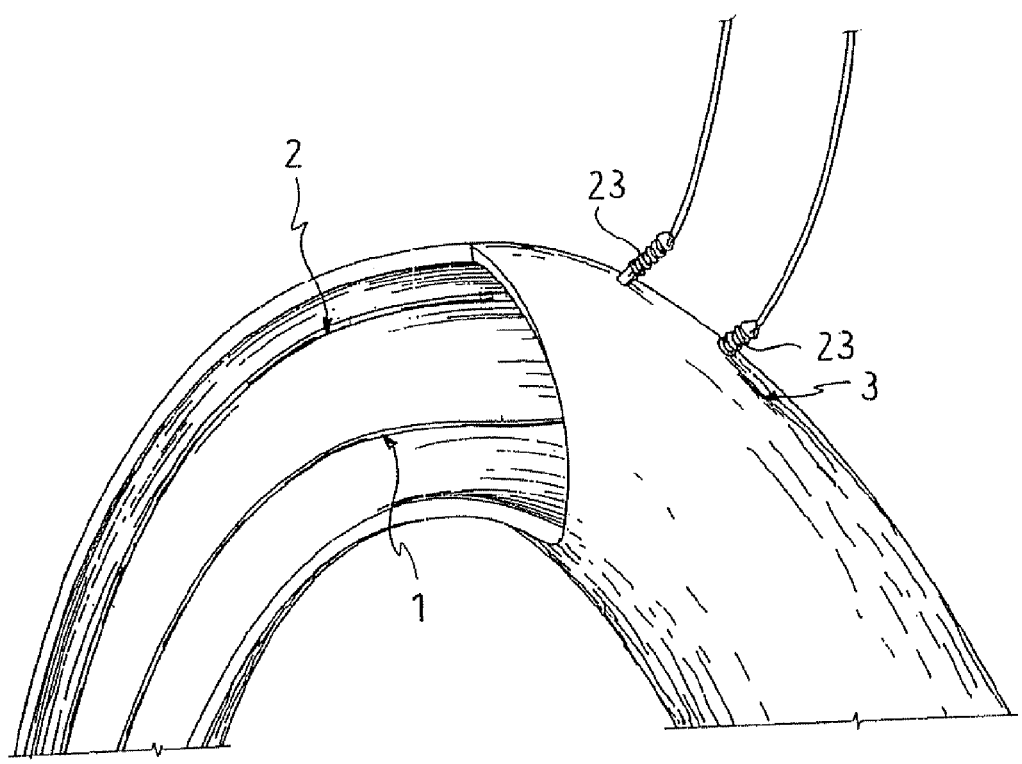
Figure 16:
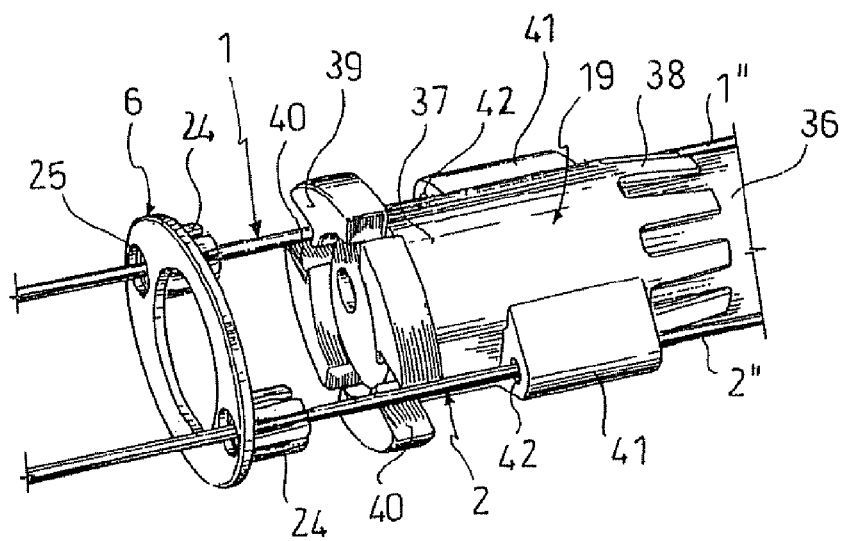
FIG. 16 is a perspective view of a distal ring of an anastomotic ring device and a surgical probe connected to a guide wire means according to the invention.
Figure 17:
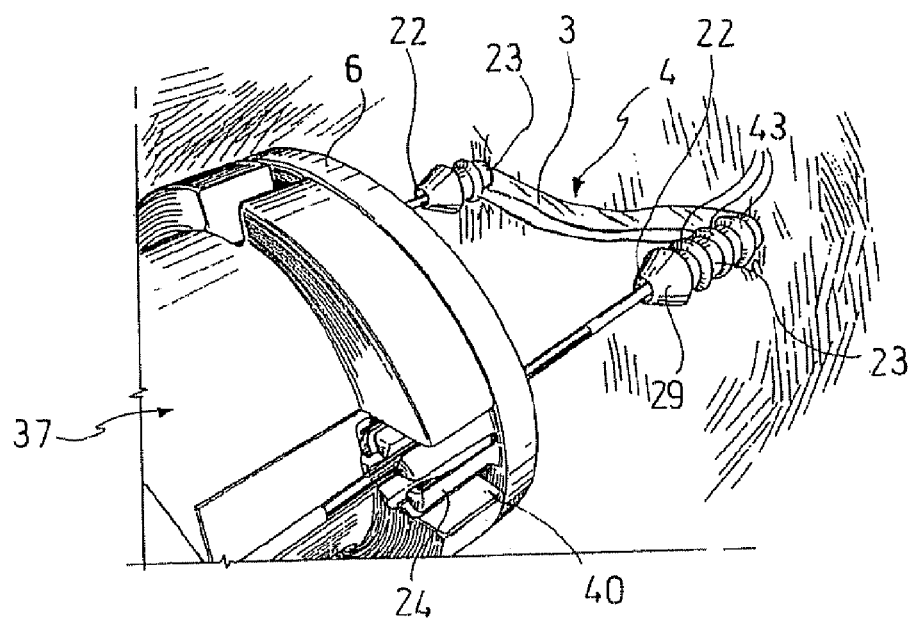
FIGS. 17 to 20 illustrate steps of a method for delivering the distal ring to a distal tissue portion and snap connect the distal and proximal ring according to the invention.
Figure 18:
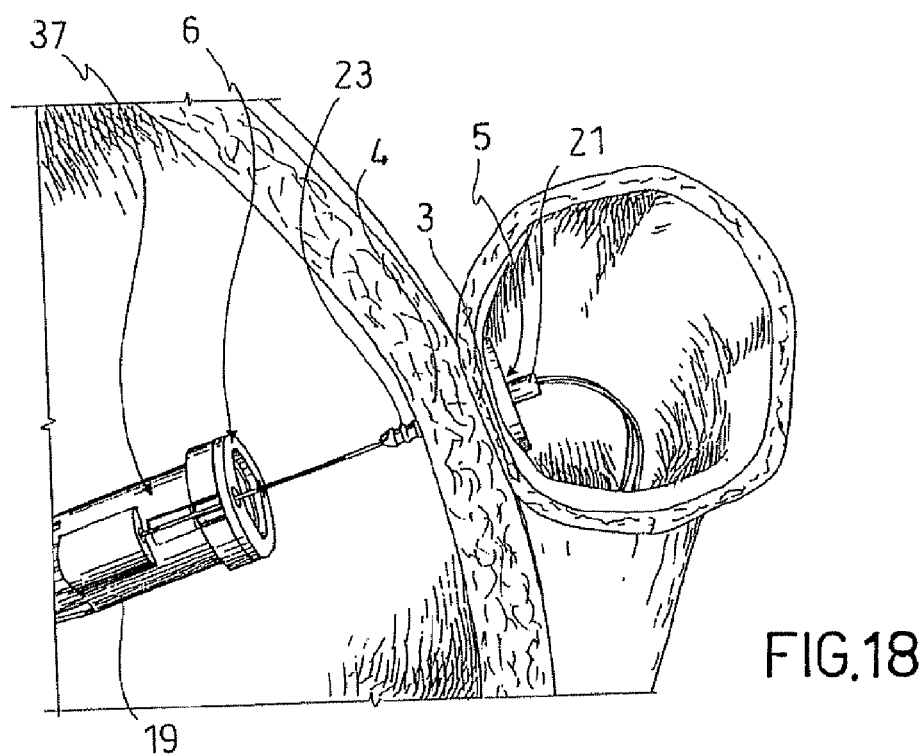
Figure 19:
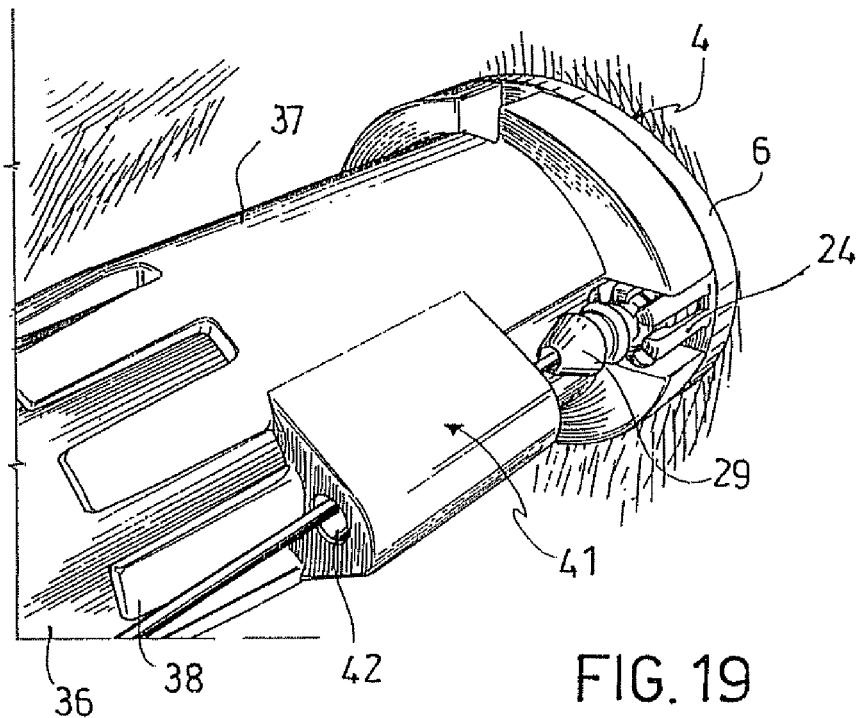
Figure 20:
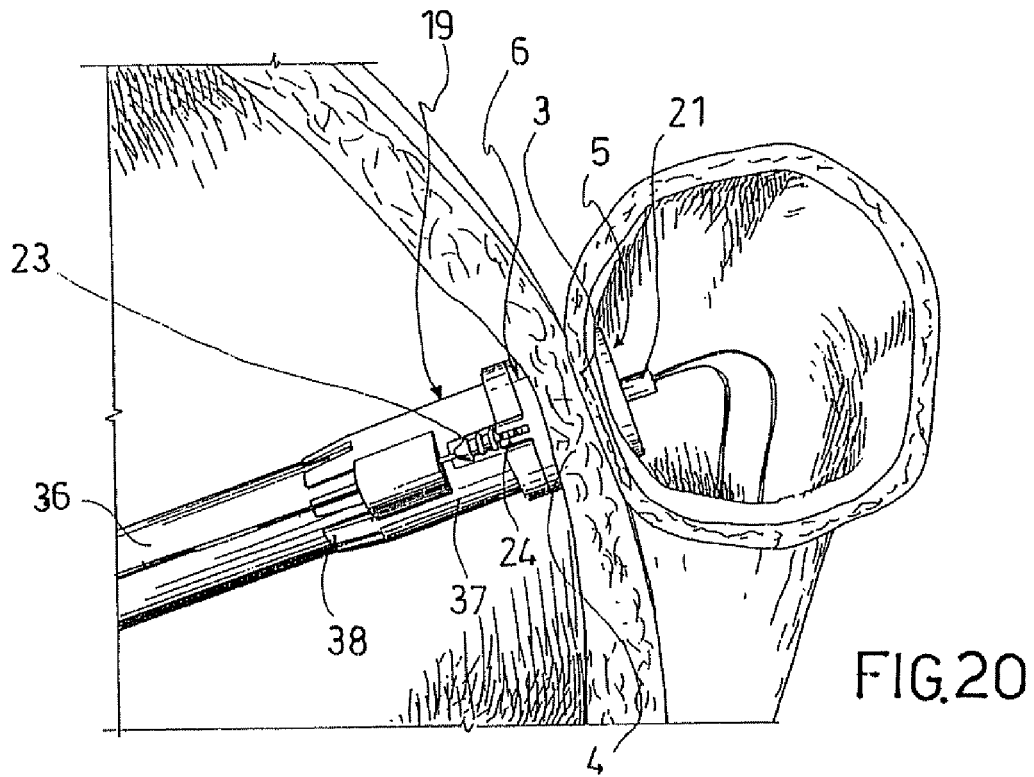
Figure 21:
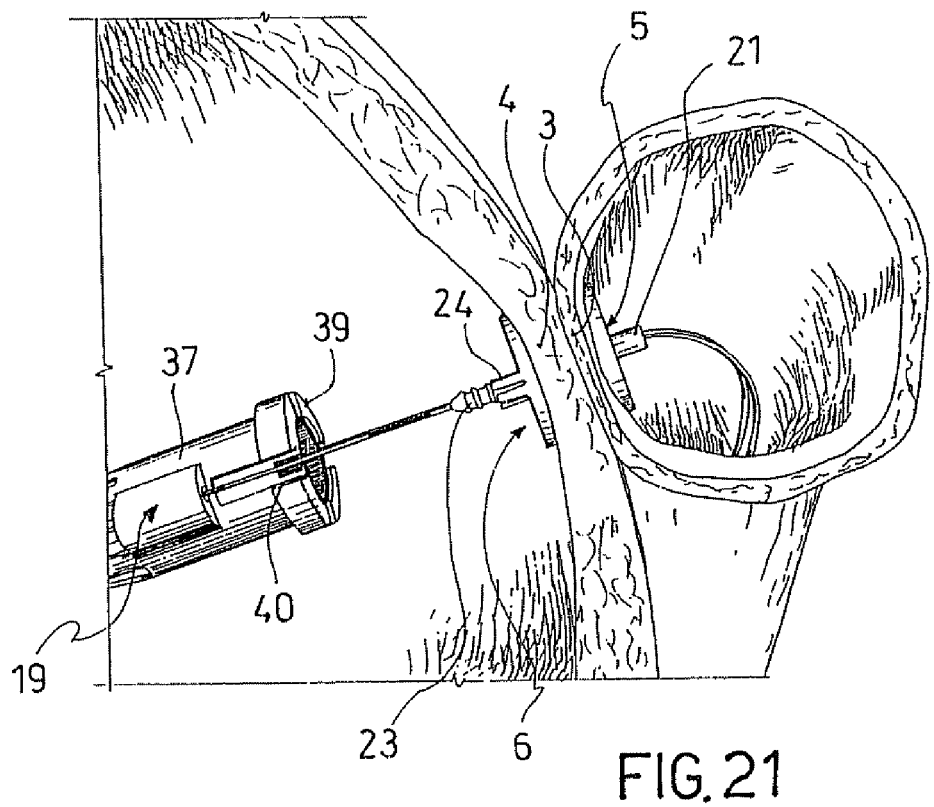
FIGS. 21 to 24 illustrate subsequent steps of the method according to the invention, in which the instrumentation is removed from the body and a gastro-jejunostomy is completed.

After having completed the guide wire loop, the proximal sheath 17 is removed from the body, thereby allowing access to the proximal guide wire portion to which the proximal ring 5 is connected by inserting the proximal guide wire ends 1', 2' through the seats 22 and clinching one of the crimpers 21 to each guide wire 1, 2 proximally behind the ring 5 (FIG. 12). By distally pulling the distal guide wire ends 1", 2" (simultaneously), the proximal ring 5 is now transported distally to the jejunum 3, wherein the ring progression is advantageously assisted by the laparoscopic grasper 13. Once arrived at the anastomotic site, the toothed pins 23 of the proximal ring are pulled through the two holes in the jejunal wall 3 so that the proximal ring is correctly placed and aligned with respect to the proximal tissue portion to be joined in anastomosis (FIGS. 13 to 15). The proximal sheath 17 is again placed over the proximal guide wire portion and the distal sheath 18 is removed from the distal guide wire portion and withdrawn from the body of the patient. The distal guide wire ends 1", 2" are now inserted through the sliding guide wire seats 25 of the distal ring 6 and through the corresponding sliding seats 42 of the deployment probe 19 (FIG. 16) and the distal ring 6 is transorally pushed by the deployment probe 19 until it reaches the gastric anastomotic site (FIG. 17, 18). By further pushing the distal ring 6 in a proximal (loop-) direction and contemporaneously pulling the distal guide wire ends 1", 2" distally, the distal and proximal rings approximate one another, align angularly and clamp the jejunal 3 and gastric wall tissue 4 between their tissue clamping surfaces 27. Upon ring approximation, the two guide wires 1, 2 still tied together by the single hole in the gastric wall 4 will open out, dissect or strap said hole, thereby aligning and finally connecting the snap connecting portions 23 of the proximal ring with the counter-snap connecting portions 24 of the distal ring 6 (FIG. 19, 20). The tissue gap, or in other words the tissue pressure can be variably adjusted by more or less intensely pulling the guide wires against the deployment probe 19. The tissue compression can be monitored by laparoscopically observing the change in tissue color.

Figure 22:
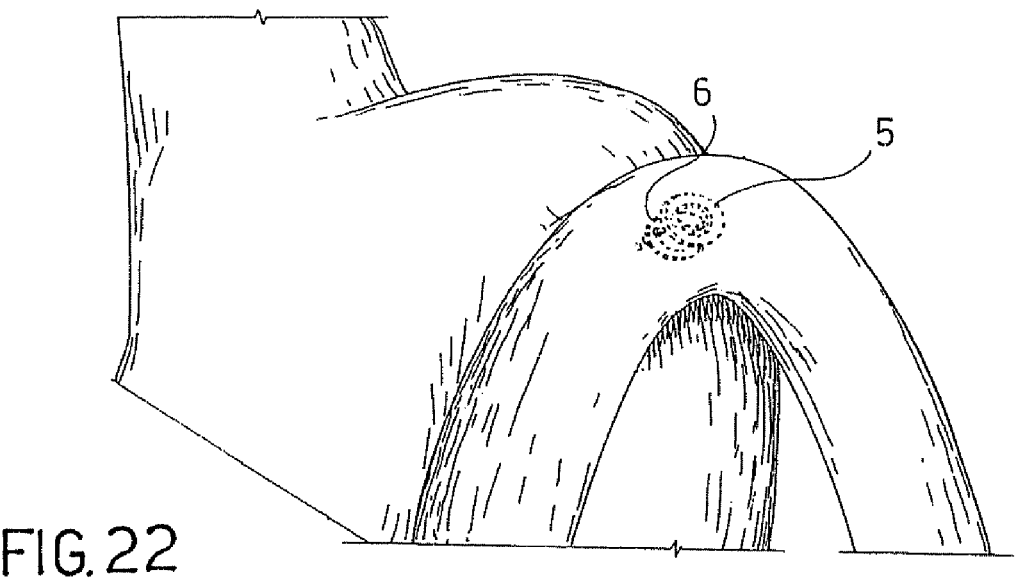
Figure 23:
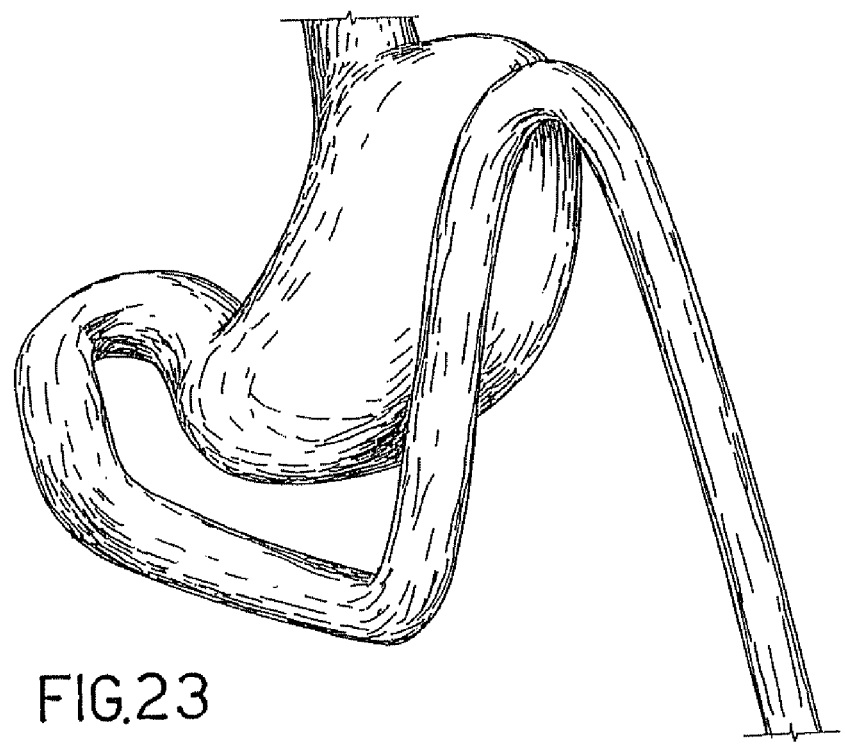
Figure 24:
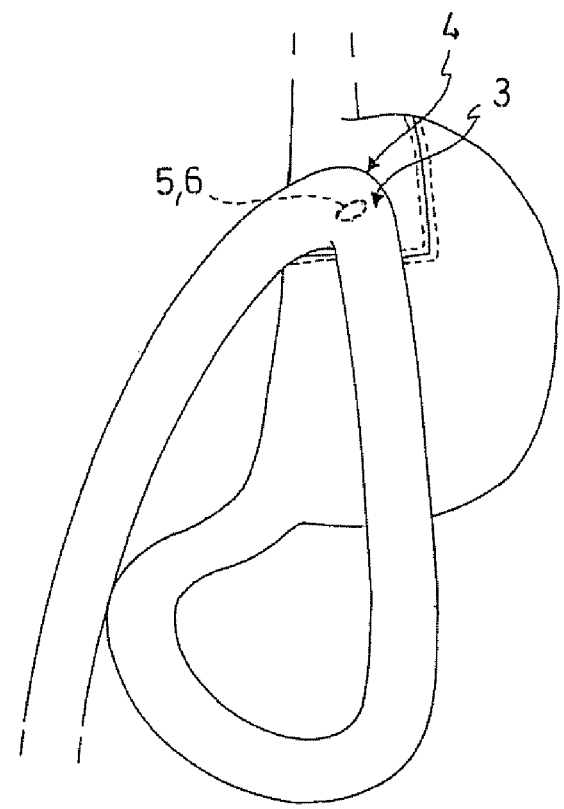

After having deployed the anastomotic ring device 5, 6, the deployment probe 19 is withdrawn transorally (FIG. 21) and the surgical probe 7 can be inserted transorally in the gastric space in order to pierce also the jejunal tissue 3 along the internal circumference of the anastomotic ring device, e.g. by means of the RF snare 11. After having extracted the surgical probe 11, the guide wires 1, 2 can be removed from the body by pulling their proximal ends 1', 2' proximally. FIGS. 22, 23 and 24 show the completed gastric-jejunal anastomosis and gastro-jejunostomy obtained by means of the above described method and by the instruments according to the invention.

Although a preferred embodiment of the invention has been described in detail, it is not the intention of the applicant to limit the scope of the claims to such particular embodiment, but to cover all modifications and alternative constructions falling within the scope of the invention.

The invention claimed is:

1. Instrumentation for performing an endoluminal or transluminal anastomosis, such as in a gastro-jejunostomy, in a jejuno-jejunostomy, in a colo-proctostomy, in a jejuno-colostomy or anastomoses of the chole duct, comprising:
    an anastomotic ring device including a proximal ring (5) having two guide wire seats (22) each of which is adapted to slidably receive one (1; 2) of two guide wires (1, 2), respectively, and a distal ring (6) having two guide wire seats (25) each of which is adapted to slidably receive one (1; 2) of said two guide wires (1, 2), respectively, the proximal ring (5) and the distal ring (6) being snap-connectable to each other,
    a surgical probe (7) comprising an elongate insertion shaft (30) and a probe head (32) distally connected to the insertion shaft (30) and adapted to be endoluminally advanced to a proximal tissue portion (3), said insertion shaft (30) defining guide wire canals (8, 9) extending into two guide wire exit openings (31) defined in the probe head (32) and adapted to deliver the distal ends (1", 2") of said guide wires (1, 2) to said proximal tissue portion (3),
    characterized in that the distance between said two guide wire exit openings (31) of the probe (7) is substantially equal to the distance between said two guide wire seats (22) of the proximal ring (5) and to the distance between said two guide wire seats (25) of the distal ring (6).

2. Instrumentation according to claim 1, further comprising a snare (11) adapted to catch the distal ends (1", 2") of the guide wires (1, 2), said snare (11) including a radiofrequency current electrode suitable to dissect and penetrate a distal tissue portion (4) of the anastomotic site,
    wherein the surgical probe (7) comprises an instrument delivery canal (12) extending into an instrument exit opening (33) defined in the probe head (32), and
    wherein said snare (11) is movable through said instrument delivery canal (12) and out of the instrument exit opening (33).

3. Instrumentation according to claim 2, wherein the instrument exit opening (33) is arranged centrally between the two guide wire exit openings (31).

4. Instrumentation according to any one of the preceding claims, wherein the proximal ring (5) comprises two snap connecting portions (23) spaced apart at a distance which is substantially equal to a distance between two corresponding counter snap connecting portions (24) provided at the distal ring (6).

5. Instrumentation according to claim 4, wherein the guide wire seats (22) of the proximal ring (5) are defined inside said snap connecting portions (23) and the guide wire seats (25) of the distal ring device (6) are defined inside said counter snap connecting portions (24), thereby aligning the axes of ring positioning and ring guidance with the axes of ring snap connection.

6. Instrumentation according to claim 1, comprising a deployment probe (19) adapted to push the distal ring (6) along said guide wires (1, 2) endoluminally to the distal tissue portion (4) of the anastomotic site, said deployment probe (19) including:
    an elongate shaft (36);
    a distal connector (37) with a proximal coupling portion (38) adapted to detachably connect with the distal end of the elongate shaft (36) and a distal push surface (39) which is at least partially complementary with an end surface of the distal ring (6) in a way that the distal ring (6) can be captively received by said push surface (39).

7. Instrumentation according to claim 6, wherein the distal connector (37) of the deployment probe (19) forms cavities (40) configured to receive with press fit distally protruding counter-snap connecting portions (24) of the distal ring (6).

8. Instrumentation according to claim 6 or 7, wherein the distal connector (37) comprises sliding seats (41) adapted to slidably receive said guide wires (1, 2).

9. Instrumentation according to claim 8, wherein said sliding seats (41) of the distal connector (37) and the guide wire seats (25) of the distal ring (6) received by the connector (37) are axially aligned.

10. Instrumentation according to claim 1, comprising a proximal sheath (17) and a distal sheath (18), both adapted to be pushed over the guide wires (1, 2) and advanced endoluminally inside the body, wherein the proximal and distal sheaths (17, 18) are visually distinguished in order to enable the surgeon to easily identify the different guide wire ends (1', 2', 1", 2").

11. Instrumentation according to claim 1, comprising a laparoscopic grasper (13) suitable to assist the endoluminal insertion of the probe (7), wherein said laparoscopic grasper (13) comprises an elongate insertion shaft (34), a distal jaw portion (35) and a proximal handle portion housing an actuation mechanism for the jaw portion (35), wherein the jaw portion (35) is configured to open wider than the external diameter of the insertion shaft (30) of said surgical probe (7).

12. A method for performing an endoluminal or transluminal anstomosis, such as e.g. a gastro-jejunostomy, a jejuno-jejunostomy, a colo-proctostomy, a jejuno-colostomy or anastomoses of the chole duct, comprising the following steps:
creating a loop of guide wire by placing a guide wire (1, 2) in the body of a patient in a way that the guide wire (1, 2) extends from an extracorporeal proximal end (1', 2') into the body where it goes through a proximal tissue portion (3) and through a distal tissue portion (4) which are planned to be joined in anastomosis and out of the body up to an extracorporeal distal end (1", 2"),
fixing a proximal ring (5) of an anastomotic ring device to the proximal end (1', 2') of the guide wire (1, 2) and delivering the proximal ring (5) to the proximal tissue portion (3) by pulling the distal extracorporeal end (1", 2") of the guide wire (1, 2) in a distal direction until the proximal ring (5) reaches the proximal tissue portion (3),
slidably connecting a distal ring (6) of the anastomotic ring device to the distal end (1", 2") of the guide wire (1, 2) and pushing it proximally along the guide wire until it reaches the distal tissue portion (4),
contemporaneously pulling the distal end (1", 2") of the guide wire (1, 2) distally and pushing the distal ring (6) proximally to approximate the proximal and distal rings, thereby tearing the proximal and distal tissue portions (3, 4) situated upon the guide wire between the distal and proximal rings (5, 6) in contact to another,
snap-connecting the distal ring (6) with the proximal ring (5), thereby clamping the distal and proximal tissue portions between them,
cutting the tissue internally overhanging the anastomotic ring device to open the anastomotic lumen,
pulling the proximal end (1', 2') of the guide wire (1, 2) to remove guide wire (1, 2) from the body,
characterized in that the endoluminal introduction of one of the guide wire (1,2) and the proximal ring (5) is assisted by laparoscopically manipulating the natural duct.

13. A method according to claim 12, wherein the step of creating the loop of the guide wire (1, 2) comprises:
transluminally introducing a slender surgical probe (7) through the proximal inlet port for the guide wire (1, 2) and pushing the probe (7) from outside the body distally towards the proximal tissue portion (3),
transporting the distal end (1", 2") of the guide wire (1, 2) to the proximal tissue portion (3) through one or more guide wire canals (8, 9) formed in the probe (7) and perforating the proximal tissue portion (3) with the guide wire end (1", 2") in a way that the distal guide wire ends (1", 2") protrude distally from the proximal tissue portion (3),
removing the surgical probe (7) from the body by pulling it proximally out of the proximal inlet port and leaving the guide wire (1, 2) in place,
transluminally introducing the same probe (7) or a different slender surgical probe through a distal inlet port for the guide wire and pushing the probe from outside the body proximally with respect to the loop direction towards the distal tissue portion (4),
transporting a radiofrequency snare (11) to the distal tissue portion (4) through an instrument delivery canal (12) formed in the probe (7) and perforating the distal tissue portion (4) by transmitting radiofrequency current from the RF snare (11) to the tissue,
subsequently passing the snare (11) through the perforation in a way that the snare (11) protrudes proximally from the distal tissue portion (4) in the same space (10) where the distal guide wire ends (1", 2") lay,
feeding the distal end (1", 2") of the guide wire (1, 2) through the snare hole and subsequently pulling the snare (11) together with the distal end (1", 2") of the guide wire (1, 2) distally through the perforation of the distal tissue portion (4) and removing the probe (7) and the snare (11) together with the distal guide wire end (1", 2") through the distal inlet port from of the body.

14. A method according to claim 13, wherein the transluminal introduction of the probe (7) to the proximal tissue portion (3) is assisted by laparoscopic manipulating the natural duct.

15. A method according to claim 13, wherein the perforation of the proximal tissue portion (3) is assisted by laparoscopically tearing the proximal tissue portion (3) against a distal tip (14) of the probe (7) defining an exit port for the guide wire (1, 2) in a way that the distal guide wire end (1", 2") poke through the tissue portion (3) in a stable and controlled manner.

16. A method according to claim 15, wherein the proximal tissue portion (3) is folded back proximally over the probe tip (14) by means of a laparoscopic grasper (13), while the probe (7) is pushed distally against the fold formed in the proximal tissue (3).

17. A method according to claim 13, wherein the distal end (1", 2") of the guide wire (1, 2) is caught by the snare (11) by grasping the guide wire end (1", 2") with a laparoscopic grasper (13) and inserting them with the grasper (13) in the snare hole under laparoscopic visualization by a laparoscope (20).

18. A method according to claim 12, wherein different loop portions are separated by visually distinguishable flexible guide wire sheaths (17, 18) along intra-corporeal zones of overlap and outside the body where said different loop portions enter the body through a same port.

* * * * *